United States Patent [19]

Ponstingl et al.

[11] Patent Number: 5,408,313
[45] Date of Patent: Apr. 18, 1995

[54] OPTICAL INTERFACE COUPLER AND SYSTEM FOR PHOTOMETRIC ANALYSIS

[75] Inventors: Michael J. Ponstingl; Robert Kessler; Walter Trump, all of St. Louis, Mo.

[73] Assignee: Custom Sample Systems, Inc., St. Louis, Mo.

[21] Appl. No.: 954,480

[22] Filed: Sep. 30, 1992

Related U.S. Application Data

[63] Continuation-in-part of Ser. No. 637,807, Jan. 7, 1991, Pat. No. 5,241,368.

[51] Int. Cl.⁶ .................... G01N 21/05; G01N 21/85
[52] U.S. Cl. .................... 356/246; 356/410; 356/440
[58] Field of Search .................... 356/246, 410, 440; 385/33, 35

[56] References Cited

U.S. PATENT DOCUMENTS

| | | | |
|---|---|---|---|
| 3,810,695 | 5/1974 | Shea | 356/73 |
| 4,343,552 | 8/1982 | Blades | 356/339 |
| 4,762,798 | 8/1988 | Deutsch | 436/67 |
| 4,786,171 | 11/1988 | Le Febre et al. | 356/246 X |
| 4,872,753 | 10/1989 | Danigel et al. | 356/246 |
| 4,988,155 | 1/1991 | Harner et al. | |
| 4,997,250 | 3/1991 | Ortiz, Jr. | 385/33 |
| 5,046,854 | 9/1991 | Weller et al. | 356/440 |
| 5,120,129 | 6/1992 | Farquharson et al. | 356/246 |
| 5,123,723 | 6/1992 | Chesnutt et al. | 385/33 |
| 5,241,368 | 8/1993 | Ponstingl et al. | 356/440 X |

OTHER PUBLICATIONS

Custom Sensors & Technology, Transmission Fiber Optic Probe Brochure, Feb. 1991.
Custom Sensors & Technology, Turbidity Fiber Optic Probe Brochure, Feb. 1991.

*Primary Examiner*—Vincent P. McGraw
*Attorney, Agent, or Firm*—Senniger, Powers, Leavitt & Roedel

[57] ABSTRACT

An optical interface coupler for coupling a flow cell to an optical absorption analyzer. The flow cell and analyzer are operable to transmit light through a fluid flowing through a chamber within the cell and analyze the transmitted light for determining certain optical properties of the fluid. The cell includes a first port through which light from a first fiber optic cable is transmitted to the chamber and a second port through which transmitted light is received and transmitted to a second fiber optic cable connected to the optical absorption analyzer. The optical interface coupler comprises a housing and a lens. The housing is releasably attachable to the cell at one of the first and second ports and defines an optical pathway therein. A cable port is in the housing for receiving one of the first and second fiber optic cables, and is in optical communication with the optical pathway. The lens is in the optical pathway spaced from the cable port and has a focal point for a given wavelength of light passing through the lens. The coupler further includes a mechanism for selectively spacing the lens relative to the cable port to control the location of the focal point of the lens relative to the cable port.

22 Claims, 3 Drawing Sheets

OPTICAL INTERFACE COUPLER AND SYSTEM FOR PHOTOMETRIC ANALYSIS

This is a continuation-in-part of U.S. patent application Ser. No. 637,807, entitled FIBER-OPTIC PROBE FOR ABSORBANCE AND TURBIDITY MEASUREMENT, filed Jan. 7, 1991, and issued Aug. 31, 1993 as U.S. Pat. No. 5,241,368.

BACKGROUND OF THE INVENTION

This invention relates generally to the measurement of various optical properties of a fluid flowing through a flow cell and, more particularly, to an optical interface coupler for coupling the flow cell to an optical absorption analyzer.

It is generally necessary to monitor optical properties, such as turbidity, of fluids used in industrial, laboratory, manufacturing, and other processes. Optical absorption analyzers, such as photometric and spectral analyzers, are commonly used for monitoring fluid flowing or circulating through a flow cell in the process stream. With such analyzers, a beam of light energy, transmitted through the fluid, is compared with a reference light source. Various properties of the fluid, such as turbidity or chemical concentrations, may be determined by this comparison. Examples of optical systems for measuring characteristics of fluids include U.S. Pat. No. 4,637,730 and U.S. Patent application Ser. No. 07/637,807 filed Jan. 7, 1991, both of which are incorporated herein by reference.

By use of fiber optic cables, the optical absorption analyzer may be located remotely from the flow cell. Remote location of the analyzer is particularly beneficial if the fluid to be monitored is hazardous or corrosive. A launch cable transmits light energy from the analyzer to the cell and a return cable transmits the light energy from the cell back to the analyzer. Lenses are typically associated with each cable so that the light energy is properly directed through the fluid stream by the launch cable and properly received by the return cable. Focusing the light through the fluid stream and on the return cable increases the amount of transmitted light collected by the return cable.

In some prior art devices, the light energy is focused by spacing the lenses from their respective cables a distance equal to the focal length of the lens. However, the focal length of a lens is dependent on the wavelength of light passing through the lens. With such lens assemblies, the distance between the lens and cable is fixed; each lens assembly can accommodate only a single wavelength of light energy. Thus, the wavelength of the light source must be known so the proper lens assembly may be selected. Such assemblies are usually expensive because manufacturers must precisely make the assemblies to meet a particular user's needs. Also, if the user changes light source or adds a filter to the light source, the focal length of the lens may change, necessitating a new assembly.

Also, such assemblies are typically sealed. As such, components of the assemblies cannot easily be removed or replaced, which may be necessary if a component fails or a design characteristic changes.

SUMMARY OF THE INVENTION

Among the objects of the present invention may be noted the provision of an improved optical interface coupler for coupling a flow cell to an optical absorption analyzer which overcomes the disadvantages and deficiencies associated with the prior art devices; the provision of such an optical interface coupler which is capable of collecting a substantial portion of light transmitted through a fluid stream; the provision of such an optical interface coupler which has an axially moveable lens to accommodate the transmission of different wavelengths of light through the lens; the provision of such an optical interface coupler in which various components may be easily removed or replaced; and the provision of such an optical interface coupler which is of relatively simple construction.

Generally an optical interface coupler of the present invention is used for coupling a flow cell to an optical absorption analyzer. The flow cell and analyzer are operable to transmit light through a fluid flowing through a chamber within the cell and analyze the transmitted light for determining certain optical properties of the fluid. The cell includes a first port through which light from a first fiber optic cable is transmitted to the chamber and a second port through which transmitted light is received and transmitted to a second fiber optic cable connected to the optical absorption analyzer. The optical interface coupler comprises a housing releasably attachable to the cell at one of the first and second ports and defining an optical pathway therein. A cable port is in the housing for receiving one of the first and second fiber optic cables. The cable port is in optical communication with the optical pathway. A lens is in the optical pathway spaced from the cable port and has a focal point for a given wavelength of light passing through the lens. The optical interface coupler further includes means for selectively spacing the lens relative to the cable port to control the location of the focal point of the lens relative to the cable port.

In another aspect of the present invention a system comprises an optical absorption analyzer employing light of a given wavelength, a flow cell, and an optical interface coupler. The flow cell is operable with the optical absorption analyzer to transmit the light through a fluid flowing through the cell and analyze the transmitted light for determining certain optical properties of the fluid. The cell includes a cell body, a chamber within the cell body through which fluid to be analyzed flows, a first port through which light from a first fiber optic cable is transmitted to the chamber, and a second port through which transmitted light is received and transmitted to a second fiber optic cable connected to the optical absorption analyzer. The optical interface coupler couples one of the first and second fiber optic cables to one of the first and second ports. The optical interface coupler includes a housing releasably attachable to the cell body at one of the first and second ports and defining an optical pathway therein. A cable port is in the housing for receiving one of the first and second fiber optic cables. The cable port is in optical communication with the optical pathway. The optical interface coupler also includes a window and a lens. The window is in the optical pathway spaced from the cable port and contacts fluid flowing through the chamber when the housing is attached to the cell and fluid is flowing through the chamber. The lens is in the optical pathway between the cable port and the window and has a focal point for the given wavelength of light. The coupler further includes means for positioning the lens relative to the cable port so that the location of the focal point of the lens is coincident with the cable port.

In still another aspect of the present invention, an optical interface coupler for coupling a flow cell to an optical absorption analyzer comprises a housing releasably attachable to the cell at one of the first and second ports and defining an optical pathway therein. A cable port is in the housing for receiving one of the first and second fiber optic cables. The cable port is in optical communication with the optical pathway. A window is in the optical pathway spaced from the cable port and contacts fluid flowing through the chamber when the housing is attached to the cell and fluid is flowing through the chamber. A lens is in the optical pathway between the cable port and the window and has a focal point for a given wavelength of light passing through the lens. The housing has first and second portions releasably secured to each other. The first portion is releasably attachable to the cell body at one of the first and second ports. The first portion holds the window and the second portion holds the lens. The window prevents fluid flowing through the chamber from entering the optical pathway so that the second portion may be detached from the first portion without affecting fluid flow through the chamber.

Other advantages and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
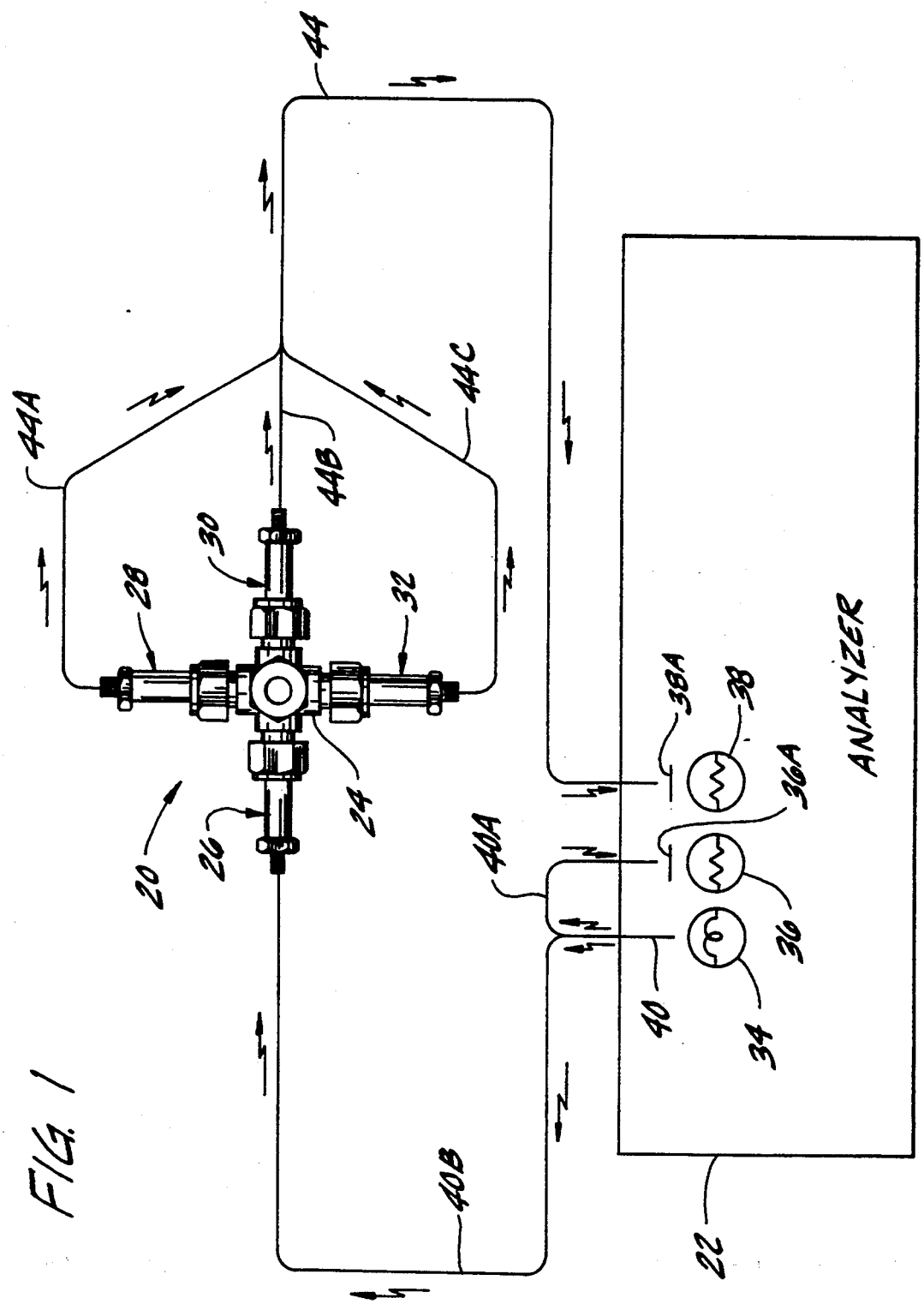
FIG. 1 is a schematic of a system of the present invention, the system having an optical absorption analyzer, a fluid cell, and four optical interface couplers.

Referring to FIG. 1, a fluid analyzing system of this invention, generally indicated at 20, is shown to include an optical absorption analyzer 22, a flow cell 24, and four optical interface couplers (OICs) 26, 28, 30, and 32. The analyzer 20 may be a photometric analyzer employing light of a particular wavelength or a spectral analyzer employing light having a broad range of wavelengths. The analyzer 22 has a source lamp 34, a reference detector 36, and a measuring detector 38. A bifurcated fiber optic cable 40 has one branch 40A which transmits a generally broad band of light from the source lamp 34 to the reference detector 36. A filter 36A filters most of the light energy so that light of only a single wavelength or only a narrow band of wavelengths is transmitted to the reference detector 36. A second branch 40B of bifurcated fiber optic cable 40 transmits light from the source lamp 34 to the OIC 26. The second branch 40B constitutes a launch cable and the OIC 26 constitutes a launch OIC for transmitting light from the source lamp 34 to the flow cell 24.

The flow cell 24 is connected in line to a fluid to be analyzed. Light energy from the launch OIC 26 illuminates the fluid flowing through the flow cell 24. Some of the light energy is absorbed or reflected by the fluid. The remaining light energy is transmitted through the flowing fluid and received by the other OICs 28, 30, and 32 (collectively, the "return OICs"), and is then transmitted through a trifurcated return fiber optic cable 44 to the measuring detector 38. A filter 38A filters the light energy before it reaches the measuring detector 38 so that only light energy of the same wavelength(s) as transmitted to the reference detector 36 is transmitted to the measuring detector 38, where the remaining filtered light energy is measured. Return OIC 30 is generally coaxial with the launch OIC 26. Return OICs 28 and 32 are generally perpendicular to the axis of the launch OIC 26 and receive light reflected by the fluid flowing through the cell 24. The return cable 44 has three branches 44A-C, each connected to one of the return OICs. In general, the analyzer 22 includes circuitry well known in the art. A signal provided by the reference detector 36 represents the intensity of light transmitted by the first branch 40A and filtered by filter 36A. A signal provided by the measuring detector 38 represents the intensity of light collected by the return OICs and transmitted by cable 44 through filter 38A. The analyzer circuitry compares the two signals to determine the characteristics of the fluid being analyzed.

Although the system 20 is shown as having three return OICs, it is to be understood that the system could have a single return OIC or any other number of OICs without departing from the scope of this invention. Also, if a single return OIC is employed, it may be positioned coaxial with or perpendicular to an axis of the launch OIC. The use of multiple return OICs, however, is particularly advantageous when measuring low levels of concentrations or turbidity.

Figure 2:
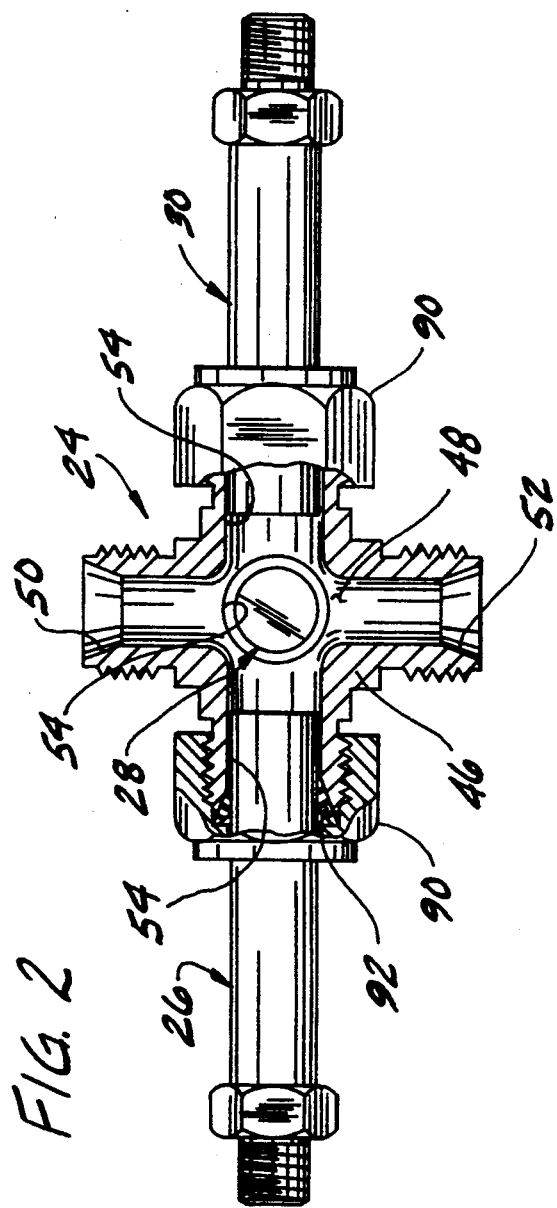
FIG. 2 is a side view of the fluid cell, in partial section, showing the connection of two optical interface couplers to the fluid cell.

As shown in FIGS. 1 and 2, the flow cell 24 includes a cell body 46, a chamber 48 within the cell body 46, a fluid inlet port 50, and a fluid outlet port 52. The fluid ports 50 and 52 are connected in-line with a conduit (not shown) which carries the fluid to be analyzed. Fluid flows from the inlet port 50, through the chamber, and out the outlet port 52. The flow cell 24 also includes four optical ports 54 (three of which are shown in FIG. 2) dimensioned for receiving the four OICs.

Figure 3:
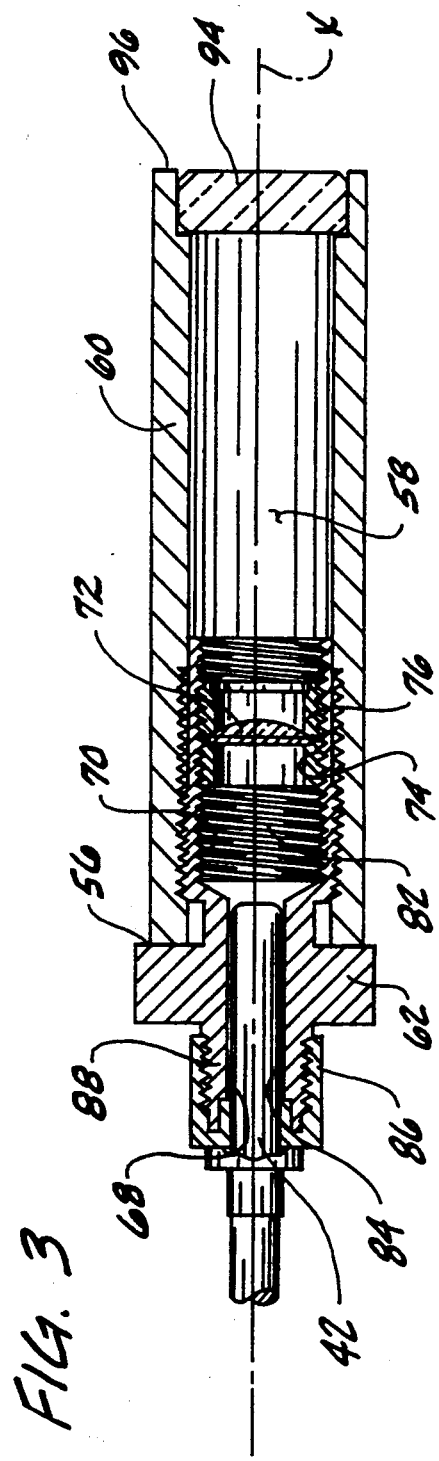
FIG. 3 is a longitudinal sectional view of one of the optical interface coupler.
Figure 4:
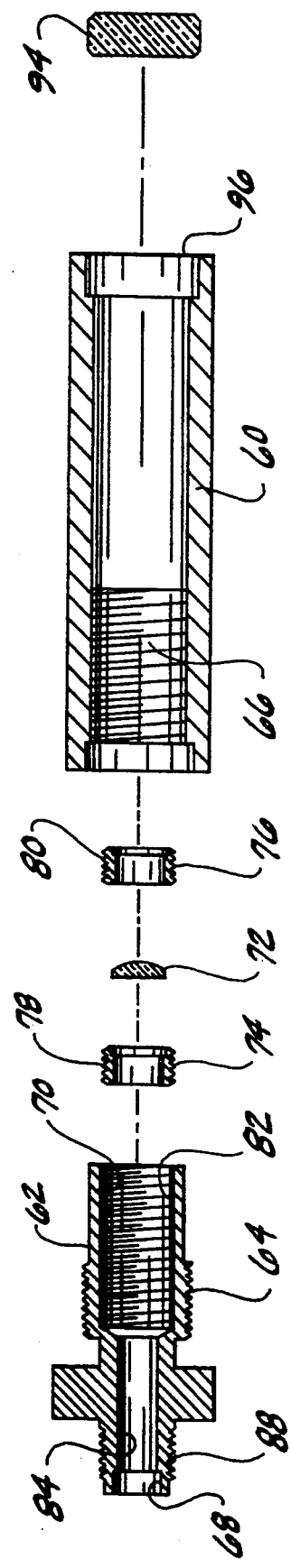
FIG. 4 is an exploded longitudinal sectional view of the optical interface coupler of FIG. 3.

For simplicity, the only OIC that will be discussed in detail is the launch OIC 26. However, it is to be understood that the return OICs 28, 30, and 32 are similarly constructed and the description of the launch OIC is equally applicable to each of them. Referring to FIGS. 2-4, the launch OIC 26 includes a housing 56 having an optical pathway 58 therein. The optical pathway 58 defines a longitudinal axis x coaxial with the path along which light energy from the launch cable 40B is transmitted. The housing 56 comprises a cylindrical sleeve 60 (constituting a first portion) and an insert 62 (constituting a second portion) adapted for insertion into the sleeve 60. The insert 62 has a thread 64 on its external surface which engages a thread 66 on the inside surface of the sleeve 60 so that the insert 62 may be screwed into and out of the sleeve 60. A cable port 68 is in the insert 62 for receiving the launch cable 40B and is in optical communication with a longitudinal bore 70 in the insert 62. The bore 70 and inside surface of the sleeve 60 are coaxial with and define the optical pathway 58.

A lens 72 is held in the bore 70 by first and second retaining rings 74 and 76. The retaining rings 74 and 76 have threads 78 and 80, respectively, which engage a thread 82 in the bore 70 such that turning of the retaining rings 74 and 76 within the bore alters the axial position of the lens 72 relative to the bore 70. The retaining rings 74 and 76 constitute retainers for connecting the lens 72 to the insert 62. Preferably, the distance between the cable port 68 and the lens 72 is equal to the focal length of the lens 72 for the wavelength of light passing therethrough to be measured by the measuring detector 38. Since the axial position of the lens 72 is adjustable, the focal point of the lens may be positioned coincident with the cable port for any wavelength of source light launched over the UV, VIS, and NIR region (220 nm through 2800 nm). Thus, the threaded retaining rings 74 and 76 and the thread 82 in the bore 70 constitute means for selectively spacing the lens 72 relative to the cable port 68 to control the location of the focal point of the lens 72 relative to the cable port 68. The precise axial position of the lens 72 relative to the bore 70 may be determined by inserting a depth probe into the distal end of the bore 70 to measure the distance between the lens 72 and the distal end of the bore 70.

It is to be understood that other means for selectively spacing the lens 72 relative to the cable port 68 could be employed. For example, the lens could be held by a tubular member slidable in the bore and axially adjustable by an adjustment screw extending through the proximal end of the insert.

As shown in FIG. 3, the cable port 68 comprises a second bore 84 into which an end of the launch cable 40B is inserted. A threaded female connector 86 is secured to the launch cable 40B and is mateable with a threaded male extension 88 on the insert 62 so that the launch cable 40B is releasably retained in the bore 84. With the cable 40B so positioned, the axial position of the lens 72 is adjusted so that the distance between the end of the cable 40B and the lens 72 is equal to the focal length of the lens 72.

Figure 5:
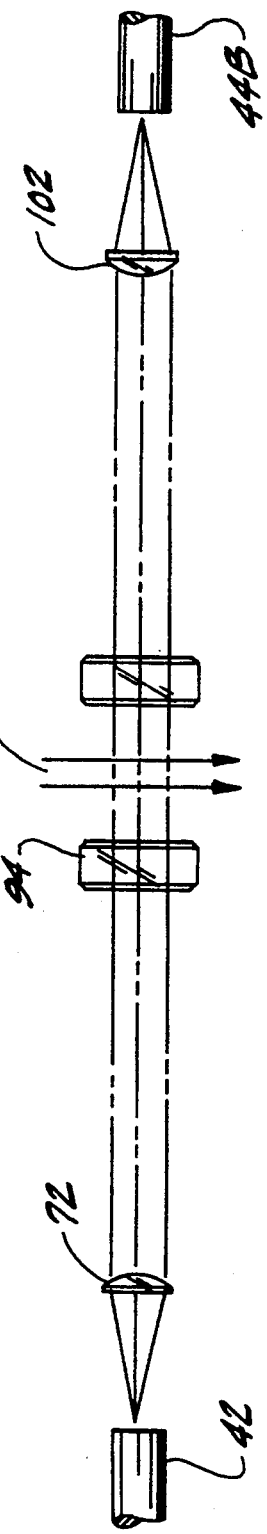
FIG. 5 is a schematic drawing illustrating the optical path of light passing through two optical interface couplers.

FIG. 5 schematically shows the optical path of light energy transmitted from the launch cable 40B through the launch OIC 28, through a fluid stream F, through a single return OIC 30 coaxial with the launch OIC 28, and then to the return branch 44B. Preferably, the launch cable 40B has a single fiber so that light emitted by its end can be considered as light from a point source. The lens 72 is positioned so that its focal point is coincident with the end of the cable 40B. The lens 72 causes parallel light to be transmitted through the fluid stream F where some of the light energy is absorbed or reflected. The remaining parallel light energy is transmitted to a lens 102 of the return OIC 30 and the lens 102 focuses the light energy on the end of a fiber in the return branch 44B. If light energy of a different wavelength is used, the lenses 72 and 102 are moved closer to or farther from their corresponding cables 40B and 44B so that the focal points of the lenses 72 and 102 are near or coincident with the ends of the cables.

As shown in FIG. 2, the sleeve 60 is slidably adjustably mounted in its corresponding optical port 54 by a lock-nut 90 threaded onto the cell body 46 and a collar 92 positioned between the lock-nut 90 and the sleeve 60. Threading the lock-nut 90 onto the cell body 46 forces the collar 92 against the sleeve 60 to lock the sleeve 60 to the flow cell 24. The axial position of the sleeve 60 in the optical port 54 may be adjusted by loosening the lock-nut 90, sliding the sleeve 60 in or out relative to the fluid chamber 48, and then re-tightening the lock-nut 90. Varying the axial position of the sleeve 60 relative to the fluid chamber 48 allows the OICs to be moved closer together or farther apart, thereby varying the path length of light passing through the chamber 48. Varying the path length allows for dynamic adjustments due to sample concentrations or molar absorptivities.

Referring again to FIGS. 3 and 4, a window member 94 is sealingly secured to the distal end 96 of the sleeve 60. When the sleeve 60 is locked to the flow cell 24 and fluid is flowing through the chamber 48, the window member 94 contacts the fluid and prevents it from entering into the optical pathway 58 and possibly fowling the lens. The window member 94 may be made of glass, quartz, sapphire, or any material that will not react with the fluid flowing through the chamber and not interfere with the light energy. Preferably, the inside surface (dry side) of the window member 94 is coated with an anti-reflection coating to increase the total energy throughput, and the outside surface (wet side) of the window member 94 is coated with Teflon ® AF, or some similar material, to render the window member 94 hydrophobic and oil resistant, thereby to prevent fouling by various aqueous solutions, oils, greases, etc.

Since the housing 56 has first arid second portions (i.e., the sleeve 60 and insert 62), various components may easily be replaced or modified. For example, if the window member 94 becomes contaminated, the sleeve 60 and window member 94 may be replaced with a new sleeve/window member assembly. Also, the lens 72 may be replaced with a lens of a different power or the position of the lens 72 with respect to the cable port 68 may be adjusted without removing the sleeve 60 from the optical port 54.

In view of the above, it will be seen that the several objects of the invention are achieved and other advantageous results attained.

As various changes could be made in the above construction without departing from the scope of the invention, it is intended that all matter contained in the above description or shown in the accompanying drawings shall be interpreted as illustrative and not in a limiting sense.

We claim:

1. An optical interface coupler for coupling a flow cell to an optical absorption analyzer, the flow cell and analyzer being operable to transmit light through a fluid flowing through a chamber within the cell and analyze the transmitted light for determining certain optical properties of the fluid, the cell including a first port through which light from a first fiber optic cable is transmitted to the chamber and a second port through which transmitted light is received and transmitted to a second fiber optic cable connected to the optical absorption analyzer, the optical interface coupler comprising:

a housing releasably attachable to the cell at one of the first and second ports and defining an optical pathway therein;

a cable port in the housing for receiving one of the first and second fiber optic cables, said cable port being in optical communication with the optical pathway;

a lens in the optical pathway spaced from the cable port and having a focal point for a given wavelength of light passing through the lens; and means for selectively spacing the lens relative to the cable port to control the location of the focal point of the lens relative to the cable port, so that the spacing of the lens from the cable port is adjustable as a function of the wavelength of light energy to be analyzed to facilitate analysis of different wavelengths of light energy.

2. An optical interface coupler as set forth in claim 1 further comprising a window in the optical pathway spaced from the cable port, said window contacting fluid flowing through the chamber when the housing is attached to the cell and fluid is flowing through the chamber, said housing including first and second portions releasably secured to each other, said first portion being releasably attachable to the cell at one of the first and second ports, said first portion holding the window and said second portion holding the lens.

3. An optical interface coupler as set forth in claim 2 wherein said window prevents fluid flowing through the chamber from entering the optical pathway.

4. An optical interface coupler as set forth in claim 3 wherein said optical pathway defines a longitudinal axis along which light is transmittable.

5. An optical interface coupler as set forth in claim 4 wherein said second portion includes a longitudinal bore coaxial with the longitudinal axis, said means for selectively spacing the lens relative to the cable port comprises means for selectively positioning the lens in the bore along said longitudinal axis.

6. An optical interface coupler as set forth in claim 5 wherein said means for selectively positioning the lens in the bore comprises an internal thread in said bore and a threaded retainer within the bore for connecting the lens to the second portion, said retainer having a thread engageable with the thread in the bore such that turning of the retainer relative to the bore alters the axial position of the lens relative to the bore.

7. An optical interface coupler as set forth in claim 1 wherein said optical pathway defines a longitudinal axis along which light is transmittable.

8. An optical interface coupler as set forth in claim 7 wherein said housing comprises a bore coaxial with the longitudinal axis, said means for selectively spacing the lens relative to the cable port comprises means for selectively positioning the lens within the bore along said longitudinal axis.

9. An optical interface coupler as set forth in claim 8 wherein said means for selectively positioning the lens within the bore comprises an internal thread in said bore and a threaded retainer within the bore for connecting the lens to the housing, said retainer having a thread engageable with the thread in the bore such that turning of the retainer relative to the bore alters the axial position of the lens relative to the bore.

10. An optical interface coupler as set forth in claim 1 wherein the cable port comprises a bore in the housing into which said one of the fiber optic cables extends, said optical interface coupler further comprising means for releasably retaining said one of the fiber optic cables in the cable port.

11. An optical interface coupler as set forth in claim 10 wherein said retaining means comprises a threaded male extension on the housing and a threaded female connector mateable with the male extension and secured to said one of the fiber optic cables.

12. A system comprising:
an optical absorption analyzer employing light of a given wavelength;
a flow cell of the type being operable with the optical absorption analyzer to transmit the light through a fluid flowing through the cell and analyze the transmitted light for determining certain optical properties of the fluid, the cell including a cell body, a chamber within the cell body through which fluid to be analyzed flows, a first port through which light from a first fiber optic cable is transmitted to the chamber, and a second port through which transmitted light is received and transmitted to a second fiber optic cable connected to the optical absorption analyzer;
an optical interface coupler for coupling one of the first and second fiber optic cables to one of the first and second ports; and
the optical interface coupler comprising:
a housing releasably attachable to the cell body at one of the first and second ports and defining an optical pathway therein;
a cable port in the housing for receiving one of the first and second fiber optic cables, said cable port being in optical communication with the optical pathway;
a window in the optical pathway spaced from the cable port, said window contacting fluid flowing through the chamber when the housing is attached to the cell and fluid is flowing through the chamber;
a lens in the optical pathway between the cable port and the window and having a focal point for the given wavelength of light; and
means for positioning the lens relative to the cable port so that the focal point of the lens is positionable coincident with the cable port for any wavelength of light energy analyzed by the optical absorption analyzer.

13. A system as set forth in claim 12 wherein said housing comprises first and second portions releasably secured to each other, said first portion being releasably attachable to the cell at one of the first and second ports, said first portion holding the window and said second portion holding the lens, said window preventing fluid flowing through the chamber from entering the optical pathway so that the second portion may be detached from the first portion without interrupting fluid flow through the chamber.

14. A system as set forth in claim 12 wherein said optical pathway defines a longitudinal axis along which light is transmittable.

15. A system as set forth in claim 14 wherein said housing comprises a bore coaxial with the longitudinal axis, said means for selectively spacing the lens relative to the cable port comprises means for selectively positioning the lens in the bore along said longitudinal axis.

16. A system as set forth in claim 15 wherein said means for selectively positioning the lens in the bore comprises an internal thread in said bore and a threaded retainer within the bore for connecting the lens to the housing, said retainer having a thread engageable with the thread in the bore such that turning of the retainer relative to the bore alters the axial position of the lens relative to the bore.

17. A system as set forth in claim 12 wherein the optical interface coupler is a first optical interface coupler for transmitting light from the first fiber optic cable through the chamber along an axis generally perpendicular to the direction of fluid flowing through the chamber, wherein the flow cell further comprises a third port through which transmitted light is received and transmitted to a third fiber optic cable connected to the optical absorption analyzer, and wherein the system further comprises:

a second optical interface coupler generally opposite the first optical interface coupler for receiving light transmitted along said axis and transmitting the received light to the second fiber optic cable;

a third optical interface coupler generally perpendicular to the axis for receiving light reflected generally perpendicular to the axis and transmitting the reflected light to the third fiber optic cable; and means for combining the light received by the second and third fiber optic cables and transmitting the combined light to the measuring detector.

18. An optical interface coupler for coupling a flow cell to an optical absorption analyzer, the flow cell and analyzer being operable to transmit light through a fluid flowing through a chamber within the cell and analyze the transmitted light for determining certain optical properties of the fluid, the cell including a first port through which light from a first fiber optic cable is transmitted to the chamber and a second port through which transmitted light is received and transmitted to a second fiber optic cable connected to the optical absorption analyzer, the optical interface coupler comprising:

a housing releasably attachable to the cell at one of the first and second ports and defining an optical pathway therein;

a cable port in the housing for receiving one of the first and second fiber optic cables, said cable port being in optical communication with the optical pathway;

a window in the optical pathway spaced from the cable port, said window contacting fluid flowing through the chamber when the housing is attached to the cell and fluid is flowing through the chamber;

a lens in the optical pathway between the cable port and the window and having a focal point for a given wavelength of light passing through the lens;

said housing having first and second portions releasably secured to each other, said first portion being releasably attachable to the cell body at one of the first and second ports, said first portion holding the window and said second portion holding the lens, said window preventing fluid flowing through the chamber from entering the optical pathway so that the second portion may be detached from the first portion without affecting fluid flow through the chamber.

19. An optical interface coupler as set forth in claim 18 further comprising means for selectively spacing the lens relative to the cable port to control the location of the focal point of the lens relative to the cable port.

20. An optical interface coupler as set forth in claim 19 wherein said optical pathway defines a longitudinal axis along which light is transmittable.

21. An optical interface coupler as set forth in claim 20 wherein said second portion includes a longitudinal bore coaxial with the longitudinal axis, said means for selectively spacing the lens relative to the cable port comprises means for selectively positioning the lens in the bore along said longitudinal axis.

22. An optical interface coupler as set forth in claim 21 wherein said means for selectively positioning the lens in the bore comprises an internal thread in said bore and a threaded retainer within the bore for connecting the lens to the first portion, said retainer having a thread engageable with the thread on the bore such that turning of the retainer relative to the bore alters the axial position of the lens relative to the bore.

* * * * *